United States Patent [19]

Höcherl et al.

[11] Patent Number: 5,060,649
[45] Date of Patent: Oct. 29, 1991

[54] ADAPTER ARRANGEMENT FOR HEART PACEMAKER LEADS

[75] Inventors: Manfred Höcherl, Rheinfelden; Jörg Reinhardt, Grenzach-Wyhlen, both of Fed. Rep. of Germany

[73] Assignee: VascoMed Institut fur Kathetertechnologie GmbH

[21] Appl. No.: 531,856

[22] Filed: May 31, 1990

[30] Foreign Application Priority Data

Jun. 2, 1989 [DE] Fed. Rep. of Germany ... 8906745[U]

[51] Int. Cl.$^5$ .............................................. A61N 1/05
[52] U.S. Cl. .................................. 128/419 P; 439/814
[58] Field of Search ...................... 128/419 P; 29/867; 439/810, 814

[56] References Cited

U.S. PATENT DOCUMENTS

| 4,316,471 | 2/1982 | Shipko et al. | 128/419 P |
| 4,466,690 | 8/1984 | Osypka | 128/419 P |
| 4,971,057 | 11/1990 | Theres | 128/419 P |

Primary Examiner—Lee S. Cohen
Assistant Examiner—Scott M. Getzow
Attorney, Agent, or Firm—Toren, McGeady & Associates

[57] ABSTRACT

An adapter arrangement for heart pacemakers includes an adapter member of an elastic, insulating material and a clamping bushing of a conductive material. The clamping bushing is surrounded by the adapter member and defines a longitudinal bore. The adapter member further defines a threaded bore which extends transversely of the longitudinal bore of the clamping bushing. A plug lead provided with a pacemaker plug is connected to the adapter member. A clamping screw can be screwed into the threaded bore. A stripping device includes a stripping holder with an lead guide shaft which is insertable in the adapter member. A stripping ring is slidingly mounted on the lead guide shaft.

7 Claims, 2 Drawing Sheets

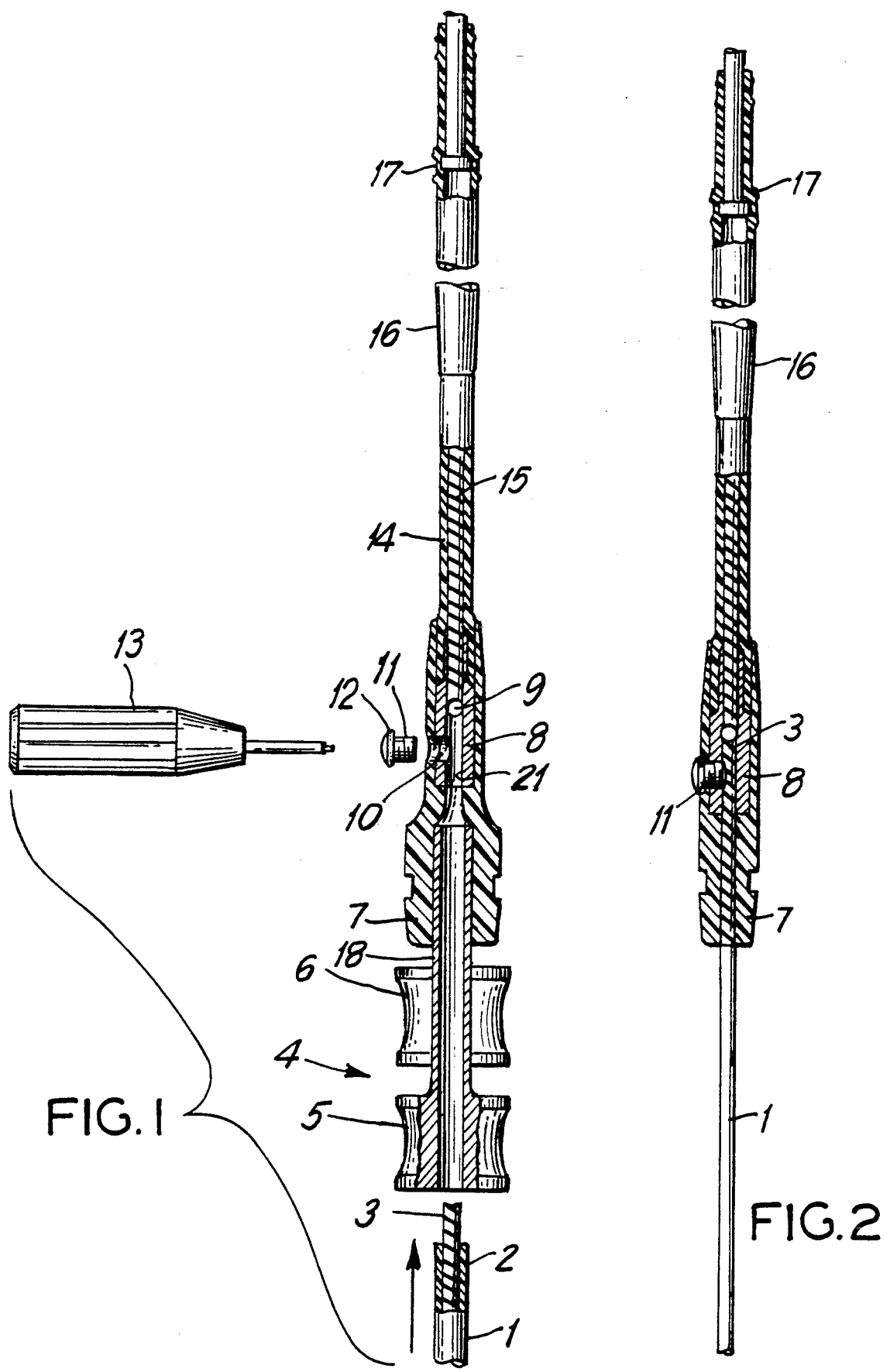

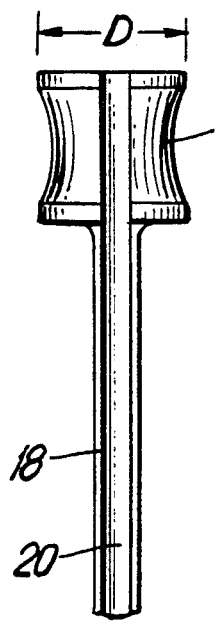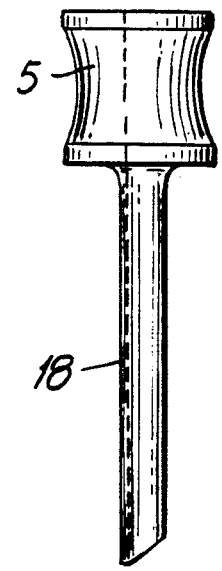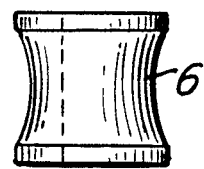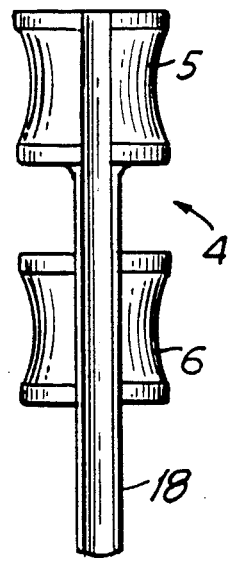
FIG.3  FIG.5  FIG.6  FIG.8
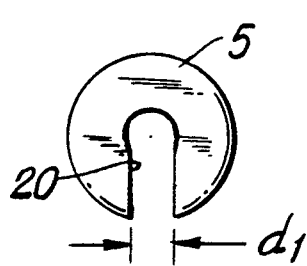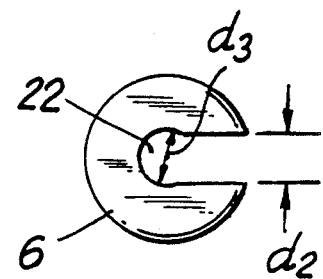
FIG.4  FIG.7

ADAPTER ARRANGEMENT FOR HEART PACEMAKER LEADS

BACKGROUND OF THE INVENTION

1. Field of the Invention

The present invention relates to an adapter arrangement for connecting an implanted heart pacemaker lead to a heart pacemaker to be implanted.

2. Description of the Related Art

Various heart pacemakers with different connector sockets are used today. In many cases, when a heart pacemaker is to be exchanged, the physician must place an adapter arrangement with fitting plug between the already implanted lead and the pacemaker. This adapter arrangement must be provided with an attaching plug which corresponds exactly to the connector socket of the pacemaker and fits together with the connector socket of the pacemaker so exactly that the system is completely tight on the lead side toward the pacemaker.

In order to obtain this tightness, the lead was in the past sealed with the adapter by manually gluing with a silicone adhesive. This method was found to be very cumbersome and impractical and problems with respect to tightness could not be excluded. Moreover, it was necessary to have in storage adapters for any possible type of plugs, so that the desired heart pacemaker selected individually for the patient could be connected to the lead. As a result, a large quantity of adapters with different plug connections had to be kept in store in hospitals. This was confusing and made storage complicated and raised the costs to hospitals.

The present invention starts from the finding that, in view of the multitude of heart pacemakers of different systems which are implanted in millions of patients, the connecting plugs will in the foreseeable future not be standardized.

For this reason, only the above-described complicated and expensive method could be used, in which final safety with respect to tightness could not be obtained. Thus, the technical solutions for exchanging heart pacemakers with implanted lead used today has to be considered unsatisfactory and in need of improvement.

SUMMARY OF THE INVENTION

It is, therefore, the primary object of the present invention to provide an arrangement of the type described above which is simple to manipulate and which, independently of the type of the connector socket of the heart pacemaker, provides a secure and absolutely tight connection between the heart pacemaker and the heart pacemaker lead.

In accordance with the present invention, an adapter arrangement of the above-described type comprises
- A. an adapter member of an elastic, insulating material, with
  - A.1 a clamping bushing of a well-conducted material, the clamping bushing having a longitudinal bore and being surrounded by the adapter member,
  - A.2 wherein a threaded bore extends through the clamping bushing and the adapter member, the threaded bore extending transversely of the longitudinal bore of the clamping bushing;
- B. a pacemaker lead connected to the adapter member and provided with a pacemaker plug;
- C. a clamping screw screwed into the transversely extending threaded bore, the clamping screw having a lens-shaped socket head cap and a threaded shaft surrounded by an 0-ring, and
  - C.1 a screwdriver which fits in the socket of the socket head cap;
- D. a stripping device, the stripping device including
  - D.1 a stripping holder with a lead guide shaft, and
  - D.2 a stripping ring which is slidably mounted on the lead drive shaft.

The adapter arrangement according to the present invention makes possible a novel and fundamentally different operating method in obtaining a tight connection between the plug lead and the pacemaker lead. The adapter arrangement proper according to the features indicated by the letter A is tightly and sealingly connected to the pacemaker lead and the pacemaker plug according to feature B.

The adapter member of elastic material is slid with its open end onto the lead guide shaft of the stripping device according to feature D until a stop is reached. As the adapter member is slid onto the lead guide shaft, the adapter member is expanded. It is now possible without difficulty to insert the end of the pacemaker lead from which a short piece of insulation has been removed, through the lead guide passage of the lead guide shaft into the longitudinal bore of the clamping bushing of the adapter member which is in axial alignment with the lead guide shaft. The end of the pacemaker lead is inserted until it practically pushes open the end of the adapter bore.

In accordance with an additional feature of the present invention, a viewing bore having approximately the same diameter as the longitudinal bore of the clamping bushing and extending transversely of this longitudinal bore is provided between the threaded bore and the beginning of the lead coil of the pacemaker lead. This feature makes it possible to monitor the insertion of the pacemaker lead by viewing, so that it is always ensured that a secure metal connection and, thus, well-conductive connection is obtained. Accordingly, the viewing bore makes it possible to observe whether the pacemaker lead has been inserted sufficiently deeply, before the lead coil is tightened in the clamping bushing absolutely tension-proof and securely by screwing in the clamping screw until the lens-shaped head of the clamping screw with the O-ring makes contact with the adapter member.

Subsequently, the stripping device is pulled out of the adapter member by means of the stripping ring of the stripping device, so that the adapter member is placed sealingly against the insulating jacket. In this manner, the novel arrangement according to the present invention makes possible a reliably conductive and sealed connection.

The various features of novelty which characterize the invention are pointed out with particularity in the claims annexed to and forming a part of this disclosure. For a better understanding of the invention, its operating advantages and specific objects attained by its use, reference should be had to the drawing and descriptive matter in which there is illustrated and described a preferred embodiment of the invention.

BRIEF DESCRIPTION OF THE DRAWING

In the drawing:

FIG. 1 is a side view, partly in section, of an adapter arrangement according to the present invention including screwdriver;

FIG. 2 is a side view, partly in section, of the adapter device of FIG. 1 with inserted pacemaker leads;

FIG. 3 is a side view of a guide shaft with holding ring of the adapter arrangement;

FIG. 4 is a top view with holding ring of the adapter device;

FIG. 5 is a side view of a guide shaft with holding ring of the adapter arrangement;

FIG. 6 is a side view of a stripping ring of the adapter arrangement;

FIG. 7 is a top view of the stripping ring of the adapter arrangement; and

FIG. 8 is a side view of a guide shaft with holding ring and stripping ring constituting the widening and insertion tool.

DESCRIPTION OF THE PREFERRED EMBODIMENT

FIG. 1 of the drawing shows an adapter arrangement according to the present invention which is used for the connection of implanted heart pacemaker leads. The plug lead 16 with the plug 17 for the heart pacemaker, not shown, includes a plug lead coil 15 which is rigidly connected to the conductive metal clamping bushing 8 and the lead 16 further includes the silicone jacket 14. The plug silicone jacket 14 is surrounded by the silicone member 7 in a liquid-tight and electrically insulating manner.

The clamping bushing 8 is provided with a longitudinal bore 21 for receiving the pacemaker lead coil 3 of the pacemaker lead 1 from which insulation has been removed. At its cylindrical outer surface the clamping bushing 8 is provided with a radially-extending threaded bore 10 for the clamping screw 11 and with a transverse viewing bore 9 which extends through the entire clamping bushing 8. The clamping screw 11 is tightened by means of the screwdriver 13. The clamping bushing 8 is surrounded by the silicone member 7 which is slid onto the guide shaft 18. The guide shaft 18 is semicircular and open. The pacemaker lead 1 with the silicone jacket can be placed in the guide shaft 18.

FIG. 2 of the drawing shows the adapter as providing the connection between the plug lead 16 and the pacemaker lead 1. The pacemaker lead 1 with the pacemaker lead coil 3 without the pacemaker silicone jacket 2 is inserted in the clamping bushing 8 which is connected to the plug lead coil 15. The clamping screw 11 with the 0-ring 12 presses against the lead spiral 3 and secures the latter against slipping out of the clamping bushing 8. The silicone member 7 rests under tension in a liquid-tight and electrically insulating manner over the silicone jacket 2 of the pacemaker lead 1.

FIGS. 3 and 5 of the drawing are side views of a guide shaft 18 and a holding ring 5 which are formed as a single member. FIG. 4 shows the guide shaft 18 and the holding ring 5 in a top view. The pacemaker lead 1 can be placed into the segment 20 of the guide shaft 18. The width $d_1$ of the segment 20 is greater than the diameter of the silicone jacket 2 of the pacemaker lead 1 which is slidable coaxially relative to the guide shaft 18 and can be placed into the segment 20 of the holding ring 5.

A stripping ring 6 is shown in FIG. 6 in a side view and in FIG. 7 in a top view. A guide bore 22 of the stripping ring 6 has a greater diameter $d_3$ than the guide shaft 18 so that the stripping ring 6 is coaxially slidable on the guide shaft 18. The gap of the stripping ring 6 has a width $d_2$ which is greater than the diameter of the pacemaker lead 1, so that the pacemaker lead 1 can be placed in the gap. The width $d_2$ is smaller than the diameter of the guide shaft 18.

FIG. 8 shows a stripping device 4 composed of the holding ring 5 and the stripping ring 6 which is axially slidable on the guide shaft 18. Since the gap of the stripping ring 6 is outwardly narrower than the greatest diameter of the guide shaft 18, the stripping ring 6 cannot be removed radially from the guide shaft 18 but must be slid on axially.

The connection of an implanted heart pacemaker lead to a heart pacemaker by means of the adapter arrangement according to the present invention is described in the following with the aid of FIG. 1.

The pacemaker lead 1 is placed in the segment 20 of the guide shaft 18 and of the holding ring 5. The stripping ring 6 is turned with its gap so that the pacemaker lead 1 can be passed through. Subsequently, the pacemaker lead 1 is moved axially relative to the guide shaft 18 until the lead coil 3, from which approximately 7 mm of the silicone jacket insulation 2 has been removed, appears in the viewing bore 9. After screwing in the clamping screw 11 by means of the screwdriver 13 for holding the lead coil 3 in the clamping bushing 8, the stripping ring 6 is slid along the guide shaft 18 away from the holding ring 5. The silicone member 7 is stripped from the guide shaft 18 and surrounds with tight contact the pacemaker silicone jacket 2 in a liquid-tight and electrically insulating manner. The setting device 4 can be reused for additional adapter devices.

While a specific embodiment of the invention has been shown and described in detail to illustrate the application of the inventive principles, it will be understood that the invention may be embodied otherwise without departing from such principles.

We claim:

1. An adapter arrangement for heart pacemakers, comprising
    an adapter member of an elastic, insulating material,
        a clamping bushing of a conductive material, the clamping bushing being surrounded by the adapter member and defining a longitudinal bore adapted for receiving a pacemaker lead,
        the adapter member defining a threaded bore extending transversely of the longitudinal bore of the clamping bushing;
        a plug lead provided with a pacemaker plug and connected to the adapter member;
        a clamping screw capable of being screwed into the threaded bore;
    a stripper comprising
        a stripping holder with lead guide shaft insertable in the adapter member, and
        a stripping ring slidably mounted on the lead guide shaft.

2. The adapter arrangement according to claim 1, wherein the clamping screw has a lens-shaped socket head cap for receiving a screwdriver, and a threaded shaft, an 0-ring being placed on the threaded shaft, the 0-ring sealing the threaded bore in a liquid-tight and electrically insulating manner.

3. The adapter arrangement according to claim 1, wherein the pacemaker lead includes a pacemaker lead coil having a diameter, and wherein the longitudinal bore of the clamping bushing has a diameter which is slightly greater than the diameter of the pacemaker lead coil.

4. The adapter arrangement according to claim 1, wherein the adapter member defines a viewing bore extending transversely of the longitudinal bore of the clamping bushing, the viewing bore having a diameter which is approximately equal to the diameter of the longitudinal bore of the clamping bushing, the plug lead including a plug lead coil having an end, the viewing bore being provided between the threaded bore and the end of the plug lead coil.

5. The adapter arrangement according to claim 1, wherein the adapter member defines a viewing bore, the viewing bore extending transversely of the longitudinal bore of the clamping bushing and having a diameter which is approximately equal to the diameter of the longitudinal bore of the clamping bushing, the viewing bore being provided between the threaded bore and the end of the longitudinal bore of the clamping bushing.

6. The adapter arrangement according to claim 1, wherein the threaded bore defines an edge, the adapter member having a sealing lip at the edge of the threaded bore for sealing the threaded bore in a liquid-tight and electrically insulating manner.

7. The adapter arrangement according to claim 6, wherein the sealing lip is a member which is integrally injection molded on the adapter member.

* * * * *